United States Patent [19]

Weiland

[11] Patent Number: 4,502,486

[45] Date of Patent: Mar. 5, 1985

[54] DEVICE FOR VETERINARY OBSTETRICAL DELIVERY

[76] Inventor: Werner Weiland, Koblenz-Olper-Str. 172, D-5413 Bendorf-Sayn, Fed. Rep. of Germany

[21] Appl. No.: 444,470

[22] Filed: Nov. 24, 1982

[30] Foreign Application Priority Data

Dec. 3, 1981 [DE] Fed. Rep. of Germany ....... 3147783

[51] Int. Cl.$^3$ ............................................ A61B 17/42

[52] U.S. Cl. .................................... 128/353; 128/361

[58] Field of Search ............... 128/352, 353, 361, 324; 403/93

[56] References Cited

U.S. PATENT DOCUMENTS

| | | | |
|---|---|---|---|
| 1,787,696 | 1/1931 | McLaren | 403/93 X |
| 3,183,911 | 5/1965 | Anglemyer | 128/353 |
| 3,870,049 | 3/1975 | Weiland | 128/352 X |

FOREIGN PATENT DOCUMENTS

| | | | |
|---|---|---|---|
| 234547 | 10/1959 | Australia | 128/352 |
| 260572 | 11/1912 | Fed. Rep. of Germany | 128/352 |
| 609883 | 8/1926 | France | 128/361 |
| 635021 | 3/1928 | France | 128/352 |
| 381918 | 10/1932 | United Kingdom | 128/352 |
| 398249 | 2/1974 | U.S.S.R. | 128/352 |

*Primary Examiner*—Michael H. Thaler
*Attorney, Agent, or Firm*—Max Fogiel

[57] ABSTRACT

Device for veterinary obstetrical delivery that can be placed against the body of the dam, that has a support (1) that is positioned in relation to the body of the dam, a rod (2) that is mounted on and can be connected to the side of the support facing away from the body, and a tensioning mechanism (3) mounted on the rod and provided with hooks (4) on which can be suspended slings for the legs of the new-born animal. To prevent injury to the subvaginal region of the body of the dam during delivery as the result of the direct action of the support, the support is mounted to pivot in one end of the rod.

6 Claims, 2 Drawing Figures

DEVICE FOR VETERINARY OBSTETRICAL DELIVERY

The invention is a device for veterinary obstetrical delivery that can be placed against the body of the dam, that has a support that is positioned in relation to the body of the dam, a rod that is mounted on and can be connected to the side of the support facing away from the body, and a tensioning mechanism mounted on the rod and provided with hooks on which can be suspended slings for the legs of the new-born animal.

A device of this type is known from, for example, German Pat. No. 1 133 076. It has a support that is positioned in relation to the body of the dam, that consists essentially of a bent piece of hard rubber or similar material with a hemispherical protuberance on the surface that is to be turned toward the dam. The hard-rubber component itself is fastened to a metal tube to which is attached a transverse tubular support by which it can be slipped rigidly onto the rod. In operation, the support is positioned immediately under the vagina, whether the dam is standing or lying down. The device as a whole is simultaneously slightly inclined. The hemispherical protuberance at the apex of the hard-rubber component allows the device to be positioned at the bottom of the dam's pelvic cavity without the support sliding down.

The design of the support plus the connection between it and the rod in accordance with the known German patent, however, involves the risk of considerable injury to the dam, especially if she is lying on the ground or floor during delivery. Attempts have accordingly been made to make the contact surface between the support and the body of the dam as large as possible, for example. If the dam is lying on the ground it is extremely likely that the associated end of the support will come into contact with the ground in such a way that the protuberance can not be inserted into the bottom of the pelvic cavity. That it can be inserted, however, is an unavoidable prerequisite for operating the tensioning mechanism on the rod. Unless this prerequisite is satisfied the dam is exposed to considerable risk of injury.

Since the support is rigidly connected to the rod, every motion of the rod is directly transferred to it. When the tensioning mechanism is activated, motions of the rod lead to nonuniformity positioning of the support in relation to the body of the dam and thus to uneven stress on the pelvic cavity. Still, it may be necessary to move the rod, when, for instance, the dam is lying on the ground and the end of the rod that faces away from her slopes down toward the ground, impeding access to the tensioning mechanism. In this case the rod will have to be raised until it is more or less horizontal.

The present invention is intended as a device for veterinary obstetrical delivery that can be supported against the body of the dam and that entails no risk of injury to the subvaginal region of the body of the dam during delivery as the result of the direct action of the support.

This objective is attained by mounting the support to pivot at one end of the rod.

The nonrigid connection of support and rod ensures that the support on the device in accordance with the invention can always be placed in a defined position at the bottom of the pelvic cavity of the dam. Only when it is in this position can problems in connection with the pelvis be avoided during delivery. Mounting the support in the rod in this way also allows the person assisting at the delivery to pivot the rod in relation to the support in such a way as to facilitate the operation. Hence, the device in accordance with the invention will ensure optimum positioning of the support in relation to the body of the dam along with optimum working conditions for the operator.

In one embodiment of the invention the support pivots around its longitudinal axis. The possibility alone of pivoting the rod around the longitudinal axis allows the operator in most applications to attain a working position from which he can employ the tensioning mechanism to optimally affect the process of birth. Pivoting around only one axis, on the other hand, ensures that the support will guide the rod in a defined path, relieving the operator of the necessity of devoting special care to the way it is positioned or guided. He can therefore devote all his attention to the dam and to the tensioning mechanism.

The support and rod are fastened together with a bolt inside the support and parallel to its longitudinal axis that fits into a hole bored across the longitudinal axis of the rod.

In one embodiment of the invention the rod snaps into the support in a position perpendicular to the surface that is in contact with the body of the dam when the device is in operation. For this purpose the support has a catch or lock facing the corresponding end of the rod and in the form of a sphere that can be thrust against the force of a spring. This will ensure an immediate and secure connection between rod and support when the rod is snapped in and facilitate handling the device when, for example, it would be redundant to pivot the rod to attain an optimal working position or when the device is to be applied to the dam. In this case folding the support down in relation to the rod would be obstructive.

The rod can always be pivoted out of the snapped-in position by 30°. This angle corresponds approximately to the position of the rod that is necessary to ensure reliable activation of the tensioning mechanism even when the dam is lying on the ground. A more obtuse angle, on the other hand, would mean that the operator would have to apply too much force to hold the rod when the leg slings were loaded, because of their angle of traction to him. There would also be a risk of the support sliding down the body of the dam.

In one embodiment of the invention the support is provided with spacers that slide without rotating through its sides against the force of springs. Arms to secure the device against the flanks of the dam extend from the outside ends of the spacers. This mechanism permits the width of the support to be reduced because it will not have to extend over the flanks of the animal itself. Thus, even when the dam is lying on the ground during birth, the end of the support that faces the ground will not be lying against it. The support is also prevented from sliding out of position, considerably reducing the risk of injury to the dam. The spacers that are mounted on the support, that slide to the side against the force of spring, and that are furnished with arms ensure that the support will be correctly positioned even when lateral forces are generated in the support by the rod.

To augment the hold of the support on the dam, especially when she is standing during birth, a strap can be introduced through the free ends of the arms. Such a strap will run through appropriate holes in the arms and rests on the back of the dam.

Other characteristics of the invention are described in the specification and in the subsidiary claims. All characteristics are separately and in combination essential to the invention.

FIG. 1 is a top view in partial section of the device for veterinary obstetrical delivery in accordance with the invention and FIG. 2 a side view.

Figure 1:
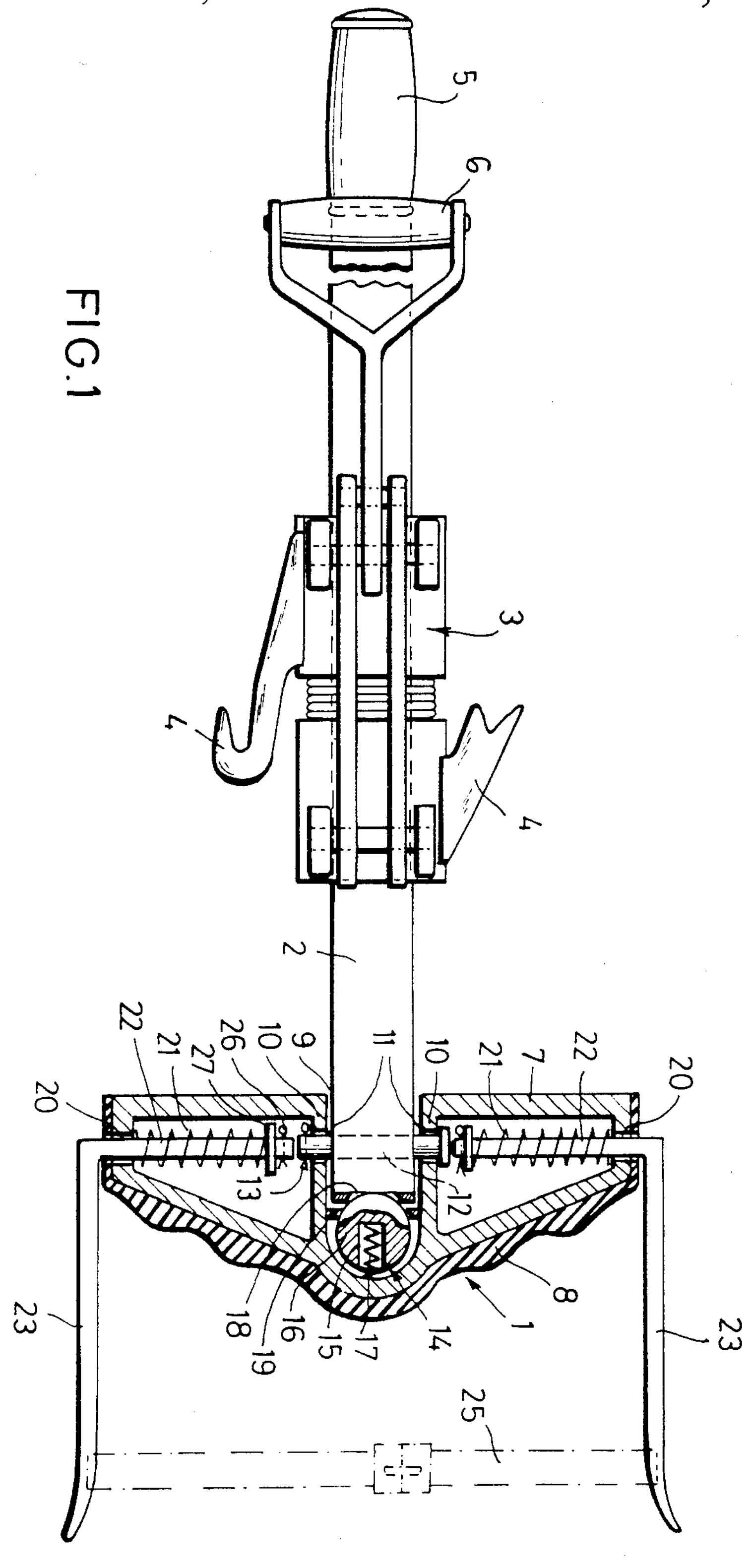
FIGS. 1 and 2 illustrate one embodiment of the invention by way of example only. The invention is not limited to this embodiment.
Figure 2:
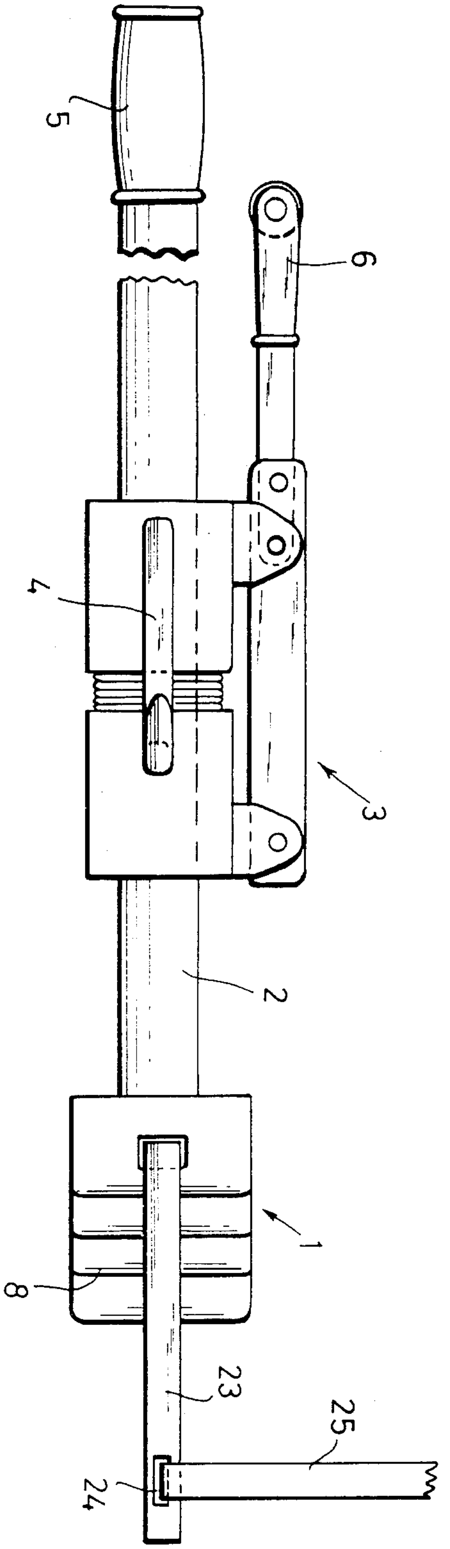

The device for veterinary obstetrical delivery in accordance with the invention consists essentially of a support 1 that is positioned in relation to the body of the dam, of a rod 2 that is mounted on and can be connected to the side of the support facing away from the body, and of a tensioning mechanism 3 mounted on the rod and with two hooks 4 on which can be suspended slings, not illustrated, for the legs of the new-born animal.

The device is held with a grip 5 on the end of rod 2 opposite support 1 and with another grip 6 on tensioning mechanism 3. Tensioning mechanism 3 is in itself not essential to the invention and hence not specified.

The surface of support 1 to be applied to the body of the dam is, as will be evident from FIG. 1, shaped like an obtuse wedge. The protuberance at the apex is employed to position the device precisely at the bottom of the dam's pelvic cavity. Support 1 itself consists of a base 7 that conforms to the overall shape of the support. Both the area that faces the body and the sides of base 7 are covered with a layer 8 of hard rubber. The surface of layer 8 that faces the body is corrugated to prevent support 1 from sliding down.

There is a recess 9 in the center of the surface of support 1 facing away from the body. Its sides are bounded by four walls 10, two of which are illustrated in FIG. 1. The other two walls are perpendicular to and connect the first two. A hole 11 is bored through each of the walls illustrated in FIG. 1. A bolt 12 runs through holes 11 and through a matching hole in rod 2, secured by a cotter pin 13.

There is a catch 14 in base 7 in the vicinity of the protuberance. Catch 14 consists of a sphere 16 with a hole 15 bored through it. A spring 17 that rests against the floor of base 7 holds sphere 16 in a recess 18 in the end of the rod 2 that faces support 1.

The figures show rod 2 in the locked position. The walls 10 that are not illustrated in FIG. 1 are far enough apart to allow rod 2 to pivot in recess 9 to an angle of approximately 30° out of the locked position. When rod 2 is in the pivoted position, a perforated plate 19 that has been forced into recess 9 prevents spring 17 from lifting sphere 16 too far off the floor of base 7.

There are holes 20 through the sides of support 1. Spacers 22 extend through holes 20. Since both have square cross-sections, spacers 22 will not rotate in holes 20. Arms 23 extend at a right angle from the outside ends of spacers 22 to position the device on the flanks of the dam. There are holes 24 at the free ends of arms 23 to receive a supporting strap 25.

Support 1 is just wide enough or, in other words, has a contact surface that is just large enough to facilitate handling of the device. Support 1 is adjusted laterally with the arms 23 on spacers 22. As will be evident from FIG. 1, spacers 22 have stops 27 that are secured with cotter pins 26 and loaded with springs 21. When arms 23 are not spread apart by outside forces, spacers 22 remain in the position illustrated in FIG. 1. To apply the device to the body of the dam arms 23 must be spread outward against the force of springs 21. When the outwards force is released, arms 23 will come to rest against the animal's flanks. This mechanism ensures that the device will be firmly attached to the animal during operation, a situation that is reinforced with the strap 25 that runs through arms 23. Finally, spring-loaded spacers 22 allow the invention to be employed with animals of various widths.

I claim:

1. Device for veterinary obstetrical delivery that can be placed against the body of a dam, comprising: a support positioned in relation to the body of the dam; a rod mounted on and connectable to the side of the support facing away from the body; tensioning means mounted on said rod and having hooks for suspending slings for legs of a new-born animal; said support being mounted pivotally in one end of said rod; said rod having means snapping into said support in a position perpendicular to the surface of the support that comes in contact with the body of the dam, said rod being swivelable out of snapped-in position perpendicular to the support after application of the device while maintaining the position of the support for preventing injury to the dam, said support being variably positionable by said rod during delivery of the new-born; said support having lock means facing the corresponding end of said rod and being in form of a sphere displaceable against the force of a spring.

2. Device as defined in claim 1, wherein said rod is always pivotable out of snapped-in position by 30°.

3. Device as defined in claim 1, including bolt means inside said support, said bolt means having a longitudinal axis parallel to said support, said rod having a bore perpendicular to the longitudinal axis of the rod, said bolt means passing through said bore.

4. Device as defined in claim 1, wherein said support has spacers; spring means, said spacers sliding without rotating through its sides against the force of said spring means; and arms for securing the device against flanks of the dam and extending from the outside ends of the spacers.

5. Device as defined in claim 4, including a strap received by free ends of said arms.

6. A device as defined in claim 1 wherein said support is mounted pivotally about its longitudinal axis.

* * * * *